US00PP18343P2

(12) United States Plant Patent
van der Zwet

(10) Patent No.: US PP18,343 P2
(45) Date of Patent: Dec. 25, 2007

(54) ***CAMPANULA* PLANT NAMED 'EMERALD'**

(50) Latin Name: *Campanula glomerata*
Varietal Denomination: Emerald

(75) Inventor: Alexius Joannes Joseph van der Zwet, Oude Wetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 11/494,095

(22) Filed: Jul. 27, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent L. Bell
(74) *Attorney, Agent, or Firm*—C. A. Whealy

(57) ABSTRACT

A new and distinct cultivar of *Campanula* plant named 'Emerald', characterized by its upright and compact plant habit; basal branching habit; freely flowering habit; and light purple-colored flowers.

2 Drawing Sheets

Botanical designation: *Campanula glomerata.*
Cultivar denomination: 'Emerald'.

BACKGROUND OF THE INVENTION

The present invention relates to a new and distinct cultivar of *Campanula,* botanically known as *Campanula glomerata* and hereinafter referred to by the name 'Emerald'.

The new *Campanula* originated from an open-pollination of an unnamed selection of *Campanula glomerata,* not patented, as the female, or seed, parent with an unknown selection of *Campanula glomerata,* as the male, or pollen, parent. The new *Campanula* was discovered and selected by the Inventor as a single flowering plant from within the progeny of the stated open-pollination grown in a controlled environment in Oude Wetering, The Netherlands in 2002.

Asexual reproduction of the new cultivar by softwood cuttings in Oude Wetering, The Netherlands, since 2004, has shown that the unique features of this new *Campanula* are stable and reproduced true to type in successive generations.

SUMMARY OF THE INVENTION

Plants of the cultivar Emerald have not been observed under all possible environmental conditions. The phenotype may vary somewhat with variations in environment such as temperature and light intensity without, however, any variance in genotype.

The following traits have been repeatedly observed and are determined to be the unique characteristics of 'Emerald'. These characteristics in combination distinguish 'Emerald' as a new and distinct cultivar:

1. Upright and compact plant habit.
2. Basal branching habit.
3. Freely flowering habit.
4. Light purple-colored flowers.

Plants of the new *Campanula* differ from plants of the female parent selection primarily in plant size and flower color.

Plants of the new *Campanula* can be compared to plants of the *Campanula* cultivar Alba, not patented. In side-by-side comparisons conducted by the Inventor in Oude Wetering, The Netherlands, plants of the new *Campanula* differed primarily from plants of the cultivar Alba in flower color as plants of the cultivar Alba had white-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Campanula.*

The photograph on the first sheet comprises a side perspective view of typical flowering plants of 'Emerald' grown in a container.

The photograph at the top of the second sheet is a close-up view of a typical inflorescence of 'Emerald'.

The photograph at the bottom of the second sheet is a close-up view of a typical leaf of 'Emerald'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photograph and following description were grown under conditions which closely approximate commercial production conditions during the summer in an outdoor nursery in Lisserbroek, The Netherlands for about two years. During the production of the plants, day temperatures ranged from 14° C. to 32° C. and night temperatures ranged from 5° C. to 15° C.

Botanical classification: *Campanula glomerata* cultivar Emerald.

Parentage:

*Female parent.*—Unnamed selection of *Campanula glomerata,* not patented.

*Male parent.*—Unknown selection of *Campanula glomerata,* not patented.

Propagation:

*Type cutting.*—Softwood cuttings.

*Time to initiate roots.*—About 20 to 30 days at 18° C.

*Time to produce a rooted young plant.*—About 100 days at 22° C.

*Root description.*—Moderately fine; light grey in color.

*Rooting habit.*—Freely branching; moderately dense.

Plant description:

*Form.*—Perennial. Upright and compact plant form; narrow inverted triangle; basal branching habit. Moderately vigorous growth habit. Campanulate flowers arranged in terminal and axillary clusters.

*Plant height.*—About 46 cm.

*Plant width.*—About 39 cm.

*Lateral branch description.*—Length: About 4.7 cm. Diameter: About 1.1 cm. Internode length: About 1.1 cm. Strength: Strong. Aspect: Upright. Texture: Roughly pubescent. Color: 143A to 143B to 144B; at the nodes, 176B.

Foliage description:

*Arrangement.*—Alternate, simple.

*Length.*—About 11.6 cm.

*Width.*—About 2.9 cm.

*Shape.*—Ovate.

*Apex.*—Broadly acute.

*Base.*—Cuneate to cordate.

*Margin.*—Serrate.

*Texture, upper and lower surfaces.*—Roughly pubescent.

*Venation pattern.*—Pinnate.

*Color.*—Developing foliage, upper surface: 137B. Developing foliage, lower surface: 137C. Fully expanded foliage, upper surface: 137A; venation, 147C. Fully expanded foliage, lower surface: 137C; venation, 147D.

*Petiole length.*—About 12.5 cm.

*Petiole diameter.*—About 6 mm.

*Petiole color, upper and lower surfaces.*—144B; towards the base, 145C to 145D.

Flower description:

*Flower arrangement and shape.*—Single campanulate flowers arranged in terminal and axillary clusters; flowers face outwardly to upright. Freely flowering, about 175 flowers per lateral branch.

*Natural flowering season.*—Continuous flowering from early June to mid-July in The Netherlands.

*Flower longevity on the plant.*—About ten days; flowers persistent.

*Fragrance.*—Faint; sweet.

*Flower buds.*—Length: About 2.5 cm. Diameter: About 1 cm. Shape: Narrowly elliptic to narrowly oblong. Color: 145C to 150C; towards the apex, N187D.

*Inflorescence size.*—Length: About 5.3 cm. Diameter: About 7.6 cm.

*Flowers.*—Diameter: About 3.4 cm. Depth (height): About 3 cm.

*Petals.*—Arrangement: Five in a single whorl; fused. Length: About 3.7 cm. Width: About 8 mm. Shape: Oblong. Apex: Acute. Margin: Entire. Texture, upper and lower surfaces: Smooth, glabrous. Color: When opening, upper surface: 75A to 75B; towards the base, 76D. When opening, lower surface: 76B to 76C; towards the base, 76D. Fully opened, upper surface: 76B to 76C; towards the base, 76D. Fully opened, lower surface: 76C; towards the base, 76C to 76D; main vein, 76B.

*Sepals.*—Arrangement: Five in a single whorl; fused. Length: About 1.9 cm. Width: About 2 mm. Shape: Narrowly lanceolate. Apex: Acute to acuminate. Margin: Entire. Texture, upper and lower surfaces: Roughly pubescent. Color: When opening, upper and lower surfaces: 143A. Fully opened, upper and lower surfaces: 143A.

*Pedicels.*—Length: About 7.8 cm. Diameter: About 4 mm. Aspect: About 25° from vertical. Strength: Strong. Texture: Smooth, glabrous. Color: 143A to 143B to 144B; tinged with 176B.

*Reproductive organs.*—Stamens: Quantity per flower: Five. Anther shape: Narrowly oblong. Anther length: About 7 mm. Anther color: 11A. Filament length: About 2 mm. Pollen amount: Moderate. Pollen color: 11B to 11C. Pistils: Quantity per flower: One. Pistil length: About 2.2 cm. Stigma shape: Tapering. Stigma color: N187B. Style length: About 2 cm. Style color: N187C. Ovary color: 144B.

*Seed/fruit.*—Seed and fruit production has not been observed.

Disease/pest resistance: Plants of the new *Campanula* have not been noted to be resistant to pathogens and pests common to *Campanula.*

Garden performance: Plants of the new *Campanula* have exhibited good tolerance to rain and wind and have been observed to be suitable for USDA Zones 3 to 9.

It is claimed:

1. A new and distinct *Campanula* plant named 'Emerald' as illustrated and described.

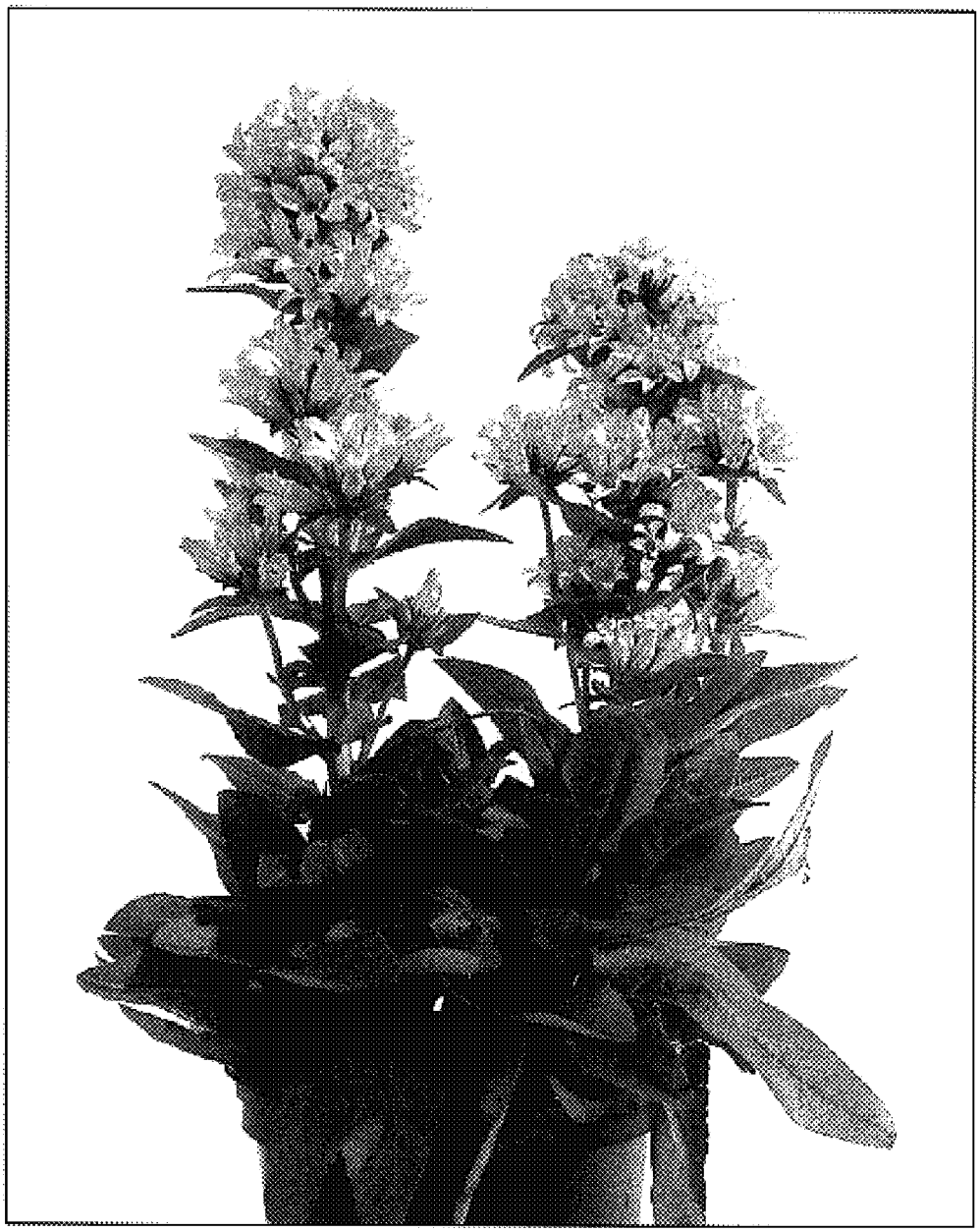

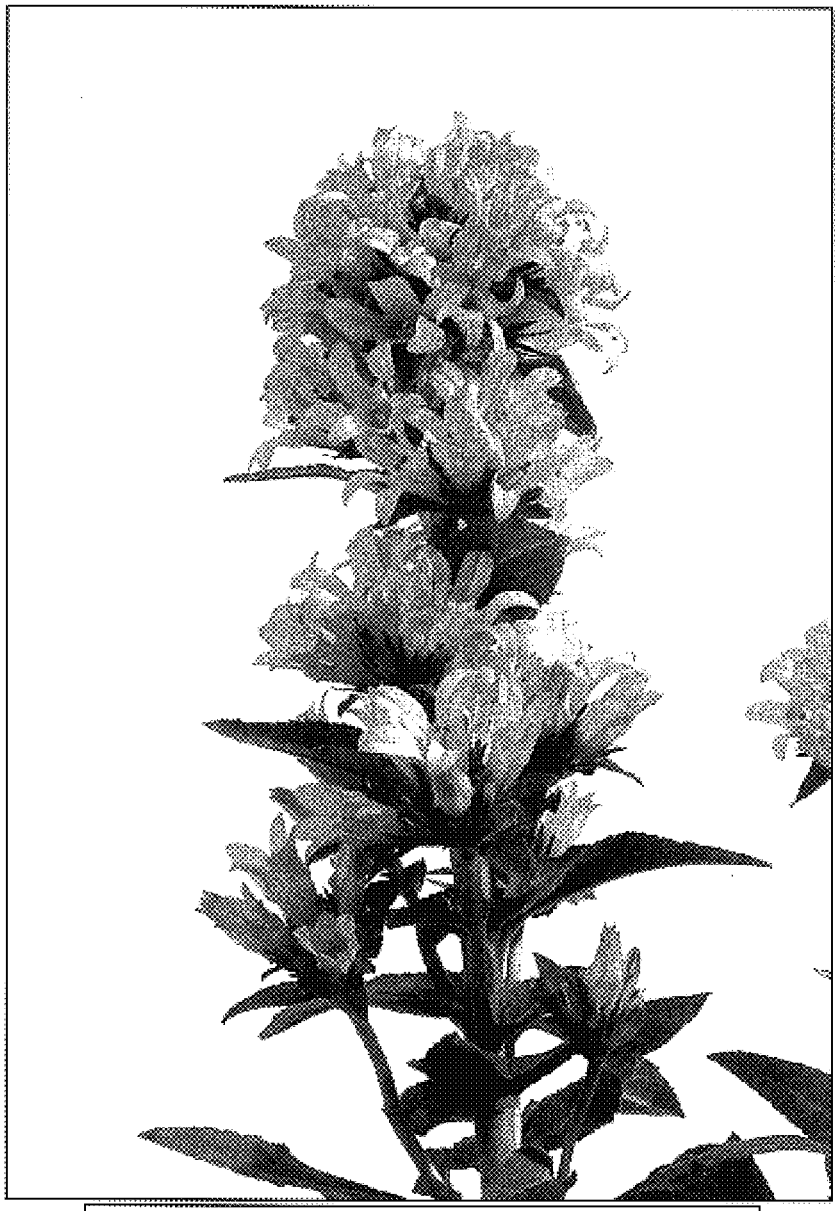
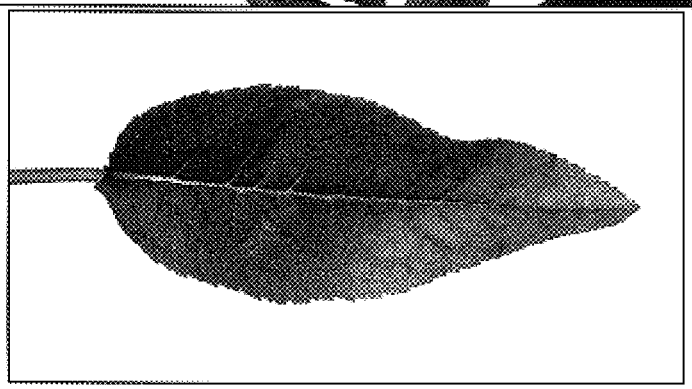

* * * * *